United States Patent [19]

Alburger

[11] 3,931,733

[45] Jan. 13, 1976

[54] METHOD AND MEANS OF ACCELERATING REMOVAL OF BACKGROUND ENTRAPMENTS IN THE INSPECTION PENETRANT PROCESS

[76] Inventor: James R. Alburger, 5007 Hillard Ave., La Canada, Calif. 91011

[22] Filed: Dec. 16, 1974

[21] Appl. No.: 532,830

[52] U.S. Cl. .............................................. 73/104
[51] Int. Cl.² ........................................ G01N 19/08
[58] Field of Search ...................................... 73/104

[56] References Cited
UNITED STATES PATENTS

| | | | |
|---|---|---|---|
| 2,806,959 | 9/1957 | Forest et al. ...................... | 73/104 X |
| 3,814,695 | 6/1974 | Molina ............................. | 73/104 X |

Primary Examiner—James J. Gill

[57] ABSTRACT

Process and apparatus for inspection penetrant detection of surface flaws in test parts in which the parts are sequentially process by the steps of (1) applying a dyed liquid penetrant to the test parts, (2) stripper-wash removal of surface penetrant, (3) interim-drying of the test parts, (4) finish-wash depletion of surface micro-entrapments of penetrant, aided by an emulsifier where applicable, (5) drying, and (6) inspection for flaw entrapment indications. The novel step of interim drying acts to alter the interaction of the finish-wash with penetrant entrapments, causing an acceleration of wash removal of the flaw entrapments and a more rapid removal of unwanted entrapments in surface porosities and micro-flaws.

5 Claims, No Drawings

3,931,733

METHOD AND MEANS OF ACCELERATING REMOVAL OF BACKGROUND ENTRAPMENTS IN THE INSPECTION PENETRANT PROCESS

RELATED PATENTS AND PATENT APPLICATIONS

U.S. Pat. No. 3,282,843 — "EMULSIFIER COMPOSITIONS".

U.S. Pat. No. 3,422,670 — "CLEANING PROCESS AND COMPOSITIONS FOR POST-EMULSIFIER INSPECTION PENETRANTS".

Application Ser. No. 431,236, filed Jan. 7, 1974, for "WATER-WASHABLE INSPECTION PENETRANT EMPLOYING MINERAL SOLVENT AND A FATTY ACID SOLUBILITY PROMOTER".

Application Ser. No. 482,465, filed June 24, 1974, for "ENHANCED STABILITY WATER-WASHABLE PENETRANT COMPOSITIONS AND PROCESS", continuation-in-part of Ser. No. 327,306, filed Jan. 29, 1973, Same Title.

Application Ser. No. 513,084, filed Oct. 8, 1974, for "WATER-WASHABLE INSPECTION PENETRANT EMPLOYING TRIGLYCERIDES AND POLYGLYCERIDES OF FATTY ACIDS".

Application Ser. No. 513,104, filed Oct. 8, 1974, for "AN OPEN-LOOP WATER-WASHABLE INSPECTION PENETRANT PROCESS".

Application Ser. No. 540,418, filed Jan. 13, 1975, for "AN INHIBITED PRE-WASH STRIPPER COMPOSITION FOR WATER-WASHABLE INSPECTION PENETRANTS".

Application Ser. No. 540,549, filed Jan. 13, 1975, for "METHOD AND MEANS OF RECOVERING AND RE-CYCLING WATER-WASHABLE INSPECTION PENETRANTS".

This invention relates to the inspection pentrant process. It is applicable to any penetrant process in which water is utilized to remove penetrant from test surfaces, but it is especially beneficial in certain water-washable penetrant processes employing the so-called "slow-solubility" water-washable penetrants to be hereinafter described.

The inspection penetrant process is employed extensively for the nondestructive testing and inspection of critical aircraft parts, such as jet engine turbine blades for example, for the presence of potential failure flaws in the nature of cracks, pinholes, inter-granular corrosion effects, and other defects or discontinuities which are open to the surface. As the process is normally carried out, a dyed liquid penetrant is applied to the parts to be tested. Application of the penetrant to test parts may be by dipping in a tank of the dyed liquid, by brushing, by pressure spray, or by electrostatic spray. The indicator dye in the liquid penetrant may be either visible-color, fluorescent, or both, in accordance with known practices.

Following application of penetrant, the test parts are allowed to stand for a few moments or a few minutes, as desired, to permit the penetrant to enter any surface defects which may be present. Then, surface penetrant is removed by a process of washing, or emulsification and washing, depending on the nature of the penetrant liquid. Entrapments of penetrant which remain in surface cracks at the completion of the wash operation are then detected by a step of inspection under white light or black light, depending on the type of indicator dye which is utilized. Usually, a step of development is employed, although this step is often considered to be a part of the inspection step.

In its simplest terms, therefore, the inspection penetrant process may be thought of as including the several steps: (1) penetrant application, (2) surface penetrant removal, and (3) inspection for residual flaw entrapments. However, this description of the process is a gross over-simplification, as will be seen from the description which follows.

For a proper understanding of the mechanisms which are involved in the inspection penetrant process, it is necessary to dissect and examine each step of the process, and to break each step down into its component elements. The basic penetrant process involves at least six steps, and sometimes seven, depending on the nature of the penetrant and whether or not a separate emulsifier is utilized.

Taking the water-washable penetrant process as a first example, the penetrant may be a self-emulsifiable composition, a water-soluble composition, or a slow-solubility composition of the type disclosed and claimed in my copending applications Ser. Nos. 431,236, 482,465, and 513,084. When a penetrant of this kind is employed, the several process steps which actually occur may be enumerated as follows: (1) penetrant application, (2) initial wash removal of surface penetrant (3) finish-wash depletion of micro-entrapments in surface porosities, (4), drying, (5) development, and (6) inspection.

It is important to note that the step of wash-removal of penetrant actually consists of two steps. Parts to which penetrant has been applied have a more-or-less thick layer of penetrant liquid on the test surfaces. When the parts are subjected to washing, the wash-removal takes place in two distinct stages. First, the bulk of the penetrant layer is removed, leaving a surface layer of porosity entrapments. This first stage has sometimes been referred to as "incubation of washing", since this incubation period must be completed before true finish-washing can take place.

Once the surface layer of penetrant has been removed, then the wash operation can act on micro-entrapments in surface porosities or micro-cracks. Naturally, some test parts have smooth surfaces which do not contain surface porosities or micro-cracks, but if such porosity conditions exist, and the process must be adapted to the existence of such surface flaws, then the washing step must be prolonged into a second stage during which micro-entrapments are depleted into the wash water.

It is essential that this second stage of washing, or finish-washing, shall be carried out to an appropriate degree, otherwise the entrapments of penetrant in surface porosities will cause an excessive background which will tend to obscure actual crack indications. The problem of unwanted background indications becomes increasingly important as the dye-performance sensitivity of the penetrant is increased, and in cases where extremely small crack indications are sought in the presence of a severe porosity condition of the test surface.

The post-emulsifier penetrant process may be considered as a second example. This process is very similar to the water-washable penetrant process, except that the penetrant is normally water-insoluble and is rendered emulsifiable by contact with a separate emulsifier composition. In modern post-emulsifier processes, the bulk of the surface penetrant is removed and recovered for re-use by means of a stripper pre-wash, thus the various steps of the process may be enumerated as follows: (1) application of penetrant, (2) initial wash-removal of penetrant (stripper pre-wash), (3) application of emulsifier to solubilize micro-entrapments, (4) finish-wash removal of emulsified penetrant, (5) drying, (6) development, and (7) inspection.

Accordingly, it is seen that the inspection penetrant process consists of a series of steps which closely follow one another in an appropriate sequence. Some of the steps may occur almost simultaneously, as for example in the water-washable penetrant process, the initial-wash and finish-wash steps normally follow one another in immediate sequence, and under the same continuing spray-wash. Also, when parts are dried, self-development begins immediately, and entrapments of penetrant begin to exude from cracks to produce visible or fluorescent indications. In some cases, a developer consisting of a dry powder or a liquid slurry of powder is applied to the test parts so as to augment the development action.

For the purpose of a proper understanding of the present invention, it is important to recognize the fact that in the inspection penetrant process, as normally used, test parts are at all times kept wet with the liquid processing materials, from the time when penetrant is first applied, up to the time when the parts are dried prior to development and inspecton. By this it is meant that the test parts are transferred from one processing bath to another, and without any drying inbetween.

It is of course possible that an inadvertant drying of parts between process steps might have occurred from time to time in the past when parts were being processed, but such drying has always been contra-indicated in the interest of rapid completion of the penetrant process.

In connection with apparatus for use in the inspection penetrant process, this normally consists of a series of process stations, which may be tanks, conveyors, drying ovens, and booths for handling or inspecting parts. Such process stations are usually arranged so that parts may be transferred from one station to the next, in sequence, with a minimum amount of delay between stations.

It will be understood, therefore, that the processing equipment, as normally used for the water-washable penetrant process consists of processing stations as follows: (1) pentrant application station, (2) initial wash station, (3) finish-wash station, (4) drying station, (5) developing station, and (6) inspection station. In the above arrangement, the initial-wash station and the finish-wash station are contained in the same wash tank, and parts are processed through these two stations without removing them from the tank. This tank may be a dip tank with agitated water or a tank or room having spray nozzles for washing and flushing the test parts. Likewise, the drying station, the developer station, and the inspection station may all be included in a single table or booth where the three process steps are carried out in immediate sequence.

In a like manner, processing equipment for carrying out the post-emulsifier process consists of process stations as follows: (1) penetrant application station, (2) pre-wash stripper station, (3) emulsifier station, (4) finish-wash station, (5) drying station, (6) developer station, and (7) inspection station. In some cases, the pre-wash stripper station and the applicable step of pre-wash stripping are omitted. The only difficulty which results from this omission is that there is a greater carry-over of penetrant into the emulsifier, and the emulsifier soon becomes contaminated and inoperative, and must be replaced.

The conventional inspection penetrant processes, as described above, exhibit the drawback that an excessive amount of background indications may be found in test parts having porous surfaces. In such test parts, it is often extremely difficult to distinguish indications of actual cracks against a background of porosity indications. I have found it possible to modify the process in such a way that background indications are selectively suppressed or removed, thereby increasing the see-ability contrast between actual crack indications and background indications. In addition, I have discovered that it is possible to improve and accelerate the wash-removal of residues of low-solubility materials from the surfaces of parts. This washing technique of the invention may be particularly advantageous in cleaning and rinsing parts which are intended to be used in contact with liquid oxygen (LOX), and which must be perfectly clean with an absolute minimum of residue material.

The principal object of the invention, therefore, is to provide a process and apparatus which will produce an acceleration of wash-removal of emulsifiable or slowly-soluble materials from the surface of parts being processed.

Another object of the invention is to provide an improvement in the conventional inspection penetrant process, whereby unwanted background indications are selectively removed.

These and other objects of the invention will in part be obvious and will in part become apparent from the following specification.

I have discovered that the introduction into the inspection penetrant process of a step of interim drying, following the initial-wash step and prior to the finish-wash step, acts to alter the interaction between the wash water (or emulsifier and wash water in the case of the post-emulsifier process), such that wash-removal is accelerated, this acceleration of washing being distinctly more pronounced in the case of minute penetrant entrapments in surface porosities or micro-cracks than for entrapments in actual cracks.

My novel step of interim drying may be employed in various ways, and more than once if desired, in a given process sequence. The essential consideration is that following the initial contact with wash water, as in a stripper initial wash, the sequence of processing must be interrupted in such a way that the test parts are dried completely before processing is resumed.

In the conventional water-washable penetrant process, parts which have been treated with penetrant are washed with water so as to first remove surface penetrant and second to deplete porosity entrapments to a degree sufficient to minimize unwanted background indications. In cases where the test parts have porous surfaces, such as are found in heat-resistant coatings on jet engine turbine blades, it is often found that depletion of the porosity background does not occur rapidly enough, and, when prolonged washing is employed, the depletion of crack entrapments takes place rapidly so that crack indications are lost by the time background indications are depleted to an acceptable level.

A similar condition results in the post-emulsifier process, where the action of prolonged contact with an emulsifier may serve to deplete porosity background indications, but at the same actual crack indications are depleted more rapidly and become lost. I have discovered that in either case, when the process sequence is interrupted by a step of interim-drying, wash removability (or emulsifier action) is accelerated. More important, this acceleration is considerably more pronounced with respect to background porosity entrapments than to actual crack entrapments. The result is that unwanted background indications are selectively removed, while actual crack indications are relatively unaffected.

The effect of interim-drying may vary in different penetrant processes, depending on the particular type of penetrant which is employed. For example, in the post-emulsifier process employing an emulsifier, the interim-drying step of the invention may be introduced following an initial stripper-wash step which is employed to remove and recover surface penetrant from test parts. Then, when an emulsifier is applied to the test parts, it is found that the emulsifier action in removing indications is more rapid than would be the case if the test parts were transferred directly from the stripper-wash to the emulsifier.

Likewise, in the conventional water-washable penetrant process, the penetrant-treated parts may be processed with an initial-wash to carry the wash removal beyond the so-called "incubation" stage. Thereafter, the washing operation may be interrupted at any point by the introduction of at least one interim-drying step of the invention, after which washing may be resumed. When this is done, it is found that wash-removal is accelerated so that the extent of background depletion is greater for a given wash-water contact time than is the case when washing is continuous, without interruption, and it is found that the see-ability of crack indications is enhanced.

The effects of wash-removal acceleration and selective background removal are especially evident when the step of interim-drying is introduced in a water-washable penetrant process employing the so-called slow-solubility water-washable penetrants. Penetrants of this kind have been disclosed and claimed in my above-mentioned U.S. patent application Ser. Nos. 431,236, 482,465, and 513,084. In general, these penetrant compositions are formulated using liquid vehicles which are only slightly soluble in water, with the result that wash-removal by diffusion-depletion from crack entrapments proceeds slowly.

When using a slow-solubility type penetrant in the process of the invention, the penetrant is applied to test parts in the conventional manner. Then, the parts are subjected to a pre-wash stripper operation in accordance with the teachings of my copending application Ser. Nos. 540,418 and 540,549. This stripper spray-wash removes the surface penetrant from the test parts within a few seconds, leaving any porosities or microcrack defects filled with penetrant.

The test parts are then withdrawn from the stripper spray-wash stage, and are dried completely. An air-knife drier may be used for this purpose, and since the pre-wash stripper is preferably operated at an elevated temperature, in the range of 100° to 140° F. or more, the parts dry rapidly. Drying is carried to completion, and the drying interval may be as little as a few seconds, or it may be several minutes. Numerous tests have indicated that a drying time of about 2 minutes is desirable, and is sufficient to establish any condition of interfacial equillibrium which may be entailed in the step of drying.

At this point in the process, it is sometimes found to be advantageous to inspect the test parts for the presence of gross cracks. Although surface porosities are filled with penetrant, yielding a pronounced background, indications of gross cracks may often be visible against the strong background. Inspection for such indications may be helpful in making judgements with regard to the relative magnitudes of surface defects.

The test parts are then transferred to a finish-wash station where washing is resumed. The wash-water contact time is controlled in this finish-wash step so as to produce a desired degree of entrapment depletion. This wash-water contact time may vary from a few seconds up to several minutes, depending on the chemistry of the slow-solubility penetrant and on its dye-performance sensitivity. For preferred penetrant compositions, the finish-wash operation may be completed in about one minute.

Finally, the test parts are removed from the finish-wash station and are transferred to a drying station. A preferred method of drying is to quickly blow off excess wash water with an air-knife or compressed-air jet. The test parts may then be developed and inspected. Self-development will occur by allowing the test parts to stand for a few minutes, whereupon entrapments in any cracks will exude to the surface of the part where they can be seen. Development may be enhanced by using a wet, dry, nonaqueous, or plastic-film developer in accordance with known practices.

The following examples illustrate how the interim-drying step of the invention may be introduced into various kinds of fluorescent inspection penetrant processes. For the purpose of evaluating the performance capabilities of the various processes, a jet engine turbine blade was selected which had a severe porosity condition in its heat-resistant coating. A faint pattern of craze-cracks was present in this coating, the magnitude of the craze-cracks being only slightly greater than the effective magnitude of the porosities in the surface. This particular turbine blade is exemplary of test parts which are extremely difficult to inspect, by virtue of the excessive amount of background porosity indications which are formed.

In each of the examples given below, the turbine blade was first processed in the normal manner, without interim-drying, and using the stated total wash-water contact time or emulsifier contact time. In every case, the background indications which were produced were so severe, even with self-development, that the craze-crack indications were almost completely obscured. When an additional developer was used, such as a conventional nonaqueous developer, the background indications developed to an intense fluorescence which completely obscured the craze-crack indications, making it quite impossible to see them at all.

EXAMPLE I

A post-emulsifier penetrant process was carried out using a fluorescent penetrant which was formulated on a water-insoluble oil vehicle, and which had a dye-performance sensitivity equivalent to Group V, as set forth in applicable Military (Air Force) penetrant material specifications. In this process, a low-energy emulsifier was utilized, this emulsifier being of the "Spray-Scrubber" type, as disclosed and claimed in my now-issued U.S. Pat. No. 3,422,670, for "CLEANING PROCESS AND COMPOSITIONS FOR POST-EMULSIFIER INSPECTION PENETRANTSP. The process steps were as follows:
1. Apply penetrant to the test blade.
2. Wash the blade in a pre-wash stripper, using a cold water spray wash.
3. Interim-dry the blade by means of compressed air, and let stand for 30 seconds to establish drying equillibrium.
4. Immerse the blade in the low-energy emulsifier for 30 seconds, then drain the test blade for 90 seconds. (Total emulsifier contact time is 2 minutes).
5. Apply a finish-rinse to remove emulsified penetrant, by spraying the blade for 30 seconds with tap water.
6. Dry the blade using compressed air.
7. Let the blade stand to self-develop for 10 minutes.
8. Inspect the blade under black light.

It was found that the introduction of the interim-drying step (step 3) resulted in an acceleration of emulsifier action and a selective removal of unwanted background indications. Inspection of the test blade under black light revealed a clearly discernible pattern of craze cracks and a relatively low level of background indications. The craze-crack pattern was found to be easily photographed, and a subsequent application of a fine spray of a conventional nonaqueous developer produced brilliant indications of the craze cracks, and these indications had good brightness contrast in comparison with the background indications.

EXAMPLE II

A water-washable penetrant process was carried out using a fluorescent penetrant of the gel-forming type, such as disclosed and claimed in my now-issued U.S. Pat. No. 3,282,843. This type penetrant, known commercially as P-136 or P-137A, is used extensively in industry for nondestructive testing of critical aerospace parts. It has a dye-performance sensitivity equivalent to Group VI of the applicable Military penetrant material specification. The process steps were as follows.
1. Apply penetrant to the test blade.
2. Wash the blade in a spray of room-temperature water for 30 seconds.
3. Interim dry the test blade by means of compressed air. Total interim-drying time, 60 seconds.
4. Finish-wash the blade in a spray of room temperature water for 60 seconds. Total wash-water contact time, 90 seconds.
5. Dry the test blade by means of compressed air.
6. Let the blade stand and self-develop for 10 minutes.
7. Inspect the blade under black light.

The process of this example was found to produce indications of the craze cracks about equivalent to the results of Example I.

EXAMPLE III

The same test blade was processed using a slow-solubility water-washable fluorescent penetrant of the type disclosed and claimed in my copending Application Ser. No. 482,465. The dye-performance sensitivity of this penetrant was about equivalent to Group VI of the applicable MIL-Specification. The sequence of process steps was as follows:
1. Apply the penetrant to the test blade.
2. Place the blade in a pre-wash stripper spray consisting of hot water (at 130° F.) saturated with dissolved penetrant, in accordance with the teachings of my copending Application Ser. No. 540,418, for "AN INHIBITED PRE-WASH STRIPPER COMPOSITION FOR WATER-WASHABLE INSPECTION PENETRANTS". Spraying time, 1 minute.
3. Interim-dry the blade, using compressed air to blow off surface liquid. Drying time, 2 minutes.
4. Apply a finish-wash using a spray of clean water at 110° F. for a total finish-wash water contact time of 1 minute.
5. Dry the blade using compressed air.
6. Let the blade stand and self-develop for 10 minutes.
7. Inspect the blade under black light.

In the process of this example, the pre-wash stripper consists of a hot saturated solution (in water) of the slow-solubility penetrant. This pre-wash solution cannot dissolve and deplete penetrant entrapments since it is already saturated with penetrant, but it can and does remove surface penetrant by the mechanical scrubbing action of the spray droplets impinging on the test surface. The hot pre-rinse also acts to heat the test part so that the part dries very rapidly during the step of interim drying. The flaw detection results obtained by use of the foregoing process was considerably superior to the results obtained in the tests of Examples I and II. The craze-crack indications were sharp and clear, and easily photographed. Background indications were reduced to a negligable amount.

EXAMPLE IV

In this example, the test penetrant used was a slow-solubility type similar to that used in Example III, except that its solubility was somewhat lower, so that its depletion time constant was somewhat greater, resulting in slower depletion-removal of crack entrapments. Dye-performance sensitivity was the same as in Examples II and III above. The step of interim-drying was conducted in multiple stages in this example, so as to illustrate the method and the results obtainable with more than one interim-drying operation. The sequence of process steps was as follows:
1. Apply the penetrant to the test blade.
2. Apply a pre-wash stripper consisting of a spray of hot (130° F.) saturated solution of the penetrant. Spray-wash for 1 minute.
3. Interim-dry for 2 minutes.
4. Wash in clean hot water for 1 minute (110° F.).
5. Interim-dry for 2 minutes.
6. Wash in clean hot water for 1 minute.
7. Interim-dry for 2 minutes.
8. Wash in clean hot water for 1 minute.
9. Interim-dry for 2 minutes.
10. Wash in clean hot water for 1 minute. Total wash time, 4 minutes.
11. Dry the blade with compressed air.
12. Let stand to delf-develop for 10 minutes.
13. Inspect under black light.

The flaw detection results obtained by use of the process of this example was about the same as was obtained in Example III above.

In all cases where the step of interim-drying was introduced, it was found that a substantial improvement was obtained in the flaw detection capability of the penetrant in the presence of a background porosity condition. For most penetrant materials, a single step of interim-drying is sufficient to produce the desired reduction of background indications. However, the invention is not limited to the use of a single step of interim-drying, and several interruptions of the washing operation by interim-drying may be employed to obtain an increasing degree of entrapment removal for a given wash-water contact time.

In Example III above, a further test was made, keeping the wash-water contact time constant at 90 seconds, but introducing an interim-drying step at each 30 second interval, a total of 3 interim-drying operations. Under such conditions, it was found that the wash-removal of crack entrapments from the blade was excessive. For the particular penetrant used in this example, a single application of interim-drying was found to be sufficient.

On the other hand, in Example IV above, the penetrant used is so slow in its solubility that a continuous wash (without interim-drying), even as long as ten minutes, fails to deplete background entrapments to a satisfactory degree, and several applications of interim-drying are necessary to produce a reduction of the background indications within a reasonable processing interval.

It will be understood that under certain circumstances, the various processing steps of the invention may all be carried out at the same physical location, and the "apparatus" used may be a single processing "station" consisting of a tank, a trough, or even a large room. For example, large aircraft wing spars may be processed in a large trough, while complete wing structures or large engine shrouds may be suspended from a chain hoist and processed in a large room having a sloping floor and a drain for collection and removal of processing liquids.

When such conditions pertain, the processing apparatus consists of a single station with respect to physical location of the test object, but the processing station is changed at each step in the process in accordance with the processing material which is utilized and the spray nozzles, air-knife apparatus, or air-gun equipment which may be brought into play. Thus, for fluorescent penetrant processing of large objects suspended in a processing room, it is merely necessary to spray on the penetrant (step 1), pre-wash strip with an inhibited hot water spray (step 2), interim-dry with compressed air or a hot-air gun (step 3), finish-wash spray with hot clean water (step 4), final-dry with an air-knife, compressed air, or a hot-air gun (step 5), let the test part hang to self-develop (step 6), and inspect under black light (step 7). All of the above operations may be carried out without moving the test part.

It will be understood that the apparatus utilized for introducing the step of interim-drying into an inspection penetrant process is preferably an air-knife or an arrangement of compressed air jets, although ovens or simple tables for air drying may be employed. It will also be understood that this interim-drying apparatus may be positioned at any convenient location near the stripper washing station and the finish washing station. A simple procedure for introducing the interim-drying step in automated processing systems is to arrange an air-knife or hot air blower above the pre-wash tank in such a way that as racks or baskets of parts are lifted out of the pre-wash, they pass through the air-knife and are quickly dried. It will be further understood that parts being processed may be subjected to interim-drying at least once or several times, that is for the purpose of this invention.

Finally, it will be understood that I make no restrictions on the duration of the period of interim-drying which is introduced into the penetrant process sequence. In many cases, it may be sufficient to dry the test parts completely, and to then immediately transfer the parts to the finish wash operation. However, I have found that when a test part is dried by the interim-drying step of the invention, washability or emulsifiability of the penetrant residues on the part undergoes a change which appears to approach an equilibrium condition on an exponential curve. Thus, for a given penetrant, the change toward interim-drying equilibrium may be 80 percent complete after 1 minute drying, 90 percent complete after 2 minutes, 95 percent complete after 5 minutes, and so on. Accordingly, where an extremely low level of residual background indications is wanted, as in cases where it is desired to use a nonaqueous developer, it may be found desirable to employ an interim-drying time interval of 5 minutes, 10 minutes, or even 30 minutes or longer. In a like manner, I make no restrictions on the operating temperatures, duration of washing, or other operational details of the penetrant process, since these are features which may be matters of preference or they may be varied in accordance with the character of parts being processed and the flaw detection results which are desired.

Although the invention has been described with reference to particular embodiments thereof, it will be understood that various changes may be made therein without departing from the spirit of the invention or the scope of the appended claims.

What is claimed is:

1. In an inspection penetrant process including the steps of (1) applying a dyed liquid water-removable penetrant to test parts so as to allow said penetrant liquid to penetrate into any surface flaws which are present, (2) washing said test parts in an initial wash to remove surface penetrant, (3) continuing the washing operation in a finish wash to deplete penetrant entrapments in surface micro-flaws, (4) drying said test parts, (5) developing indications of penetrant entrapments in surface flaws, and (6) inspecting said test parts for visual indications of dyed penetrant entrapments, the improvement consisting of the introduction of at least one step of interim-drying of said test parts following said initial wash and prior to said finish wash.

2. An inspection penetrant process in accordance with claim 1, in which said dyed liquid penetrant is a water-insoluble emulsifiable composition, and a step of emulsifier application is introduced following said improvement-step of interim-drying and prior to said finish-washing step.

3. An inspection penetrant process in accordance with claim 1, in which said dyed liquid penetrant is a slow-solubility composition composition having a solubility in water within the range of from about 0.001 to about 3 percent.

4. In an apparatus sequentially employed as enumerated, for treating test parts by the inspection penetrant process, including (1) apparatus for penetrant application, (2) apparatus for stripper-wash removal of surface penetrant, (3) apparatus for finish-wash depletion of entrapments of penetrant in surface micro-flaws, (4) apparatus for final drying of said test parts, (5) apparatus for development of indications, and (6) apparatus for inspecting and examining said test parts for the presence of flaw indications, the improvement consisting of apparatus for interim-drying of said test parts, said interim-drying apparatus being introduced into the said sequentially-employed apparatus following said apparatus for stripper-wash removal of surface penetrant, and ahead of said apparatus for finish-wash depletion of entrapments of penetrant in surface micro-flaws.

5. Apparatus in accordance with claim 4, in which apparatus for emulsifier application is introduced into said sequentially-employed apparatus following said improvement interim-drying apparatus, and ahead of said apparatus for finish-wash depletion of entrapments of penetrant in surface micro-flaws.

* * * * *